United States Patent [19]

Marciel

[11] Patent Number: Plant 7,455

[45] Date of Patent: Feb. 26, 1991

[54] ROSE PLANT NAMED DEVLOREN

[75] Inventor: Stanley G. Marciel, Aptos, Calif.

[73] Assignee: DeVor Nurseries, Inc., Watsonville, Calif.

[21] Appl. No.: 383,614

[22] Filed: Jul. 24, 1989

[51] Int. Cl.[5] ..... A01H 5/00
[52] U.S. Cl. ..... Plt./18
[58] Field of Search ..... Plt./18, 17

*Primary Examiner*—Howard J. Locker
*Attorney, Agent, or Firm*—Charles W. Rummler

[57] ABSTRACT

A new and distinct greenhouse rose variety particularly distinguished by its continuous and profuse production of large flowers of a scarlet and primrose coloration carried on long, strong upright stems on a plant of medium height having a vigorous free branching growth habit with abundant foliage.

1 Drawing Sheet

BACKGROUND OF THE NEW PLANT

This new rose variety originated as a seedling of a hybrid produced by me by my crossing the variety Emily Post (U.S. Plant Pat. No. 3,749) with the variety Prominent (U.S. Plant Pat. No. 3,380) as the pollen parent. The present plant having been selected from seedlings of the said hybrid because of the large size of its blooms of scarlet to crimson coloration and its apparently vigorous, upright growth habit and I propagated this selected seedling in greenhouse at Pleasanton, Calif. by budding with very satifactory results so that propagation was carried on through several successive generations which demonstrated clearly that the distinctive characteristics of this plant would be carried on from generation to generation and appeared to be firmly fixed.

DESCRIPTION OF THE DRAWING

My new rose plant is illustrated by the accompanying photographic drawing which shows a three-quarter face view of a half-opened bloom together with a newly opened bud and a bud near to opening to commercial size, the colors shown being as close to those herein specified as is reasonably possible to obtain by professional photographic procedures.

DESCRIPTION OF THE NEW VARIETY

The following is a detailed description of my new greenhouse rose plant based upon observation of plants grown in greenhouse at Pleasanton, Calif., with the color designations being according to The R.H.S. Colour Chart published by The Royal Horticultural Society of London, England.

THE PLANT

Origin: Seedling.

Parentage:

*Seed parent.*—Emily Post (U.S. Plant Pat. No. 3,749).

*Pollen parent.*—Prominent (U.S. Plant Pat. No. 3,380).

Classification:

*Botanic.*—Greenhouse Rose.

Form: Upright free branching bush.

Height: About 65 to 75 cm.

Color of cane: Yellow green, 146B.

Foliage:

*Quantity.*—Abundant.

*Number of Leaves.*—8 or 9, from last flower cut, averaging about 117 mm. long and of odd-pinnate shape.

*Leaflets.*—Number: 3 or 5. Size: About 75 to 80 mm. long and about 50 to 53 mm. wide. Shape: Ovate with denticulate margins. Texture: Leathery. Aspect: Smooth and semi-glossy.

*Color.*—Upper side —·Green, 137B. Under side — Green, 143B with greyed purple, 185C.

*Petioles.*—Size: About 12 to 15 mm.

Ribs and veins: Depressed on upper side and slightly protruding on the underside.

Rachis:

*Length.*—About 30 mm. on 3 leaflet leaves and about 60 to 75 mm. on 5 leaflet leaves.

Character: Smooth with small spines on underside.

Thorns:

*Size.*—About 6 to 8 mm. long.

*Color.*—Yellow green, 144B with tips of greyed red, 178A.

THE BUD

Size (commercial): Large.
*Diameter.*—About 39 to 41 mm.
*Depth.*—About 33 to 38 mm.
Shape: Slender and tapering toward base.
Rate of opening: Slow.
Color of Petals:
*When sepals first divide.*—Crimson, 52A with yellow green, 154C, at the base.
*When petals being to unfurl.*—Scarlet, 43C with yellow, 4C at the base.
Sepals:
*Number.*—Five.
*Shape.*—Lanceolate.
*Character.*—The sepals curl back as the flower opens.
*Color.*—Inside — Yellow green, 147D. Outside — Green, 143C with touches of greyed purple, 185B.
Calyx:
*Shape.*—Funnel-shaped.
*Size.*—Medium and broad.
*Splitting.*—Calyx does not split.
*Aspect.*—Smooth.
Peduncle of flower stem:
*Length.*—About 12 to 13 cm.
*Character.*—Erect, rigid and hairy with small, slender spines.
*Color.*—Yellow green, 146B.

THE FLOWER

Blooming habit: Continuous and profusely the year around under glass.
Size of bloom: Large.
*Diameter.*—(When bloom is half-opened) about 86 mm.
*Depth.*—About 50 mm.
Borne: Singly.
Shape:
*When bloom first opens.*—Cup-shaped with high center.
*When bloom matures.*—Petals spread into wide cup.
Petalage:
*Number.*—25 to 27.
*Arrangement.*—Uniformly imbricated.
*Form.*—Generally orbicular with acute tip.
*Texture.*—Leathery.
*Appearance.*—Satiny.
*Color.*—Outer petals: Upper side: Body — Scarlet, 43C with base of yellow, 4C. Reverse side: Body — Scarlet, 43D with margin of 43C and base of yellow, 154D. Inside petals: Upper side: Body — Crimson, 52A with base of yellow green, 154C. Reverse side: Body — Rhodomine red, 51A with base of green, 150C.

Petaloids:
*Number.*—4 to 6.
*Size.*—About 20 mm. long.
*Color.*—Rhodomine red, 52B with base of yellow, 4C.
Peduncle of flower stem:
*Length.*—About 12 to 13 cm.
*Color.*—Yellow green, 144A.
*Character.*—Sturdy and upright.
Discoloration after full bloom: Moderate.
Persistence: The petals stay on the stem for 12 to 14 days.
Fragrance: Light raspberry.
Disease resistance: Moderately resistant to mildrew, rust, and black spot as observed at Pleasanton, Calif.
Lasting quality: Long-lasting on the plant and moderately lasting as a cut flower in vase keeping.

THE REPRODUCTION ORGANS

Stamens:
*Number.*—About 1 to 7.
*Arrangement.*—Slightly introse.
*Anthers.*—Size: About 2 mm. Color: Yellow orange, 19A.
*Filaments.*—Length: About 5 mm. Color: Green white, 157B.
*Pollen.*—Color: Yellow orange, 19A.
Pistils:
*Number.*—About 86.
*Styles.*—Length: About 10 to 12 mm. Color: Orange, 27C at the bottom and red, 36A at the top.
*Stigmas.*—Color: Yellow, 11B.
Character of the ovaries: Medium funnel-shaped with rounded edges and flattened in center with a covering of silver threads.
Fertility: This variety is very fertile. The hips are pear shaped and their color at maturity is orange 26-A.

This variety most nearly resembles Emily Post, but is distinguished by having a longer and sturdier stem and a larger and more elegant flower with a deeper red coloration and petals that have slightly ruffled edges.

I claim:

1. The new and distinct variety of greenhouse rose plant substantially as herein shown and described, characterized by its profuse and continuous production of flowers of large size and scarlet to crimson coloration.

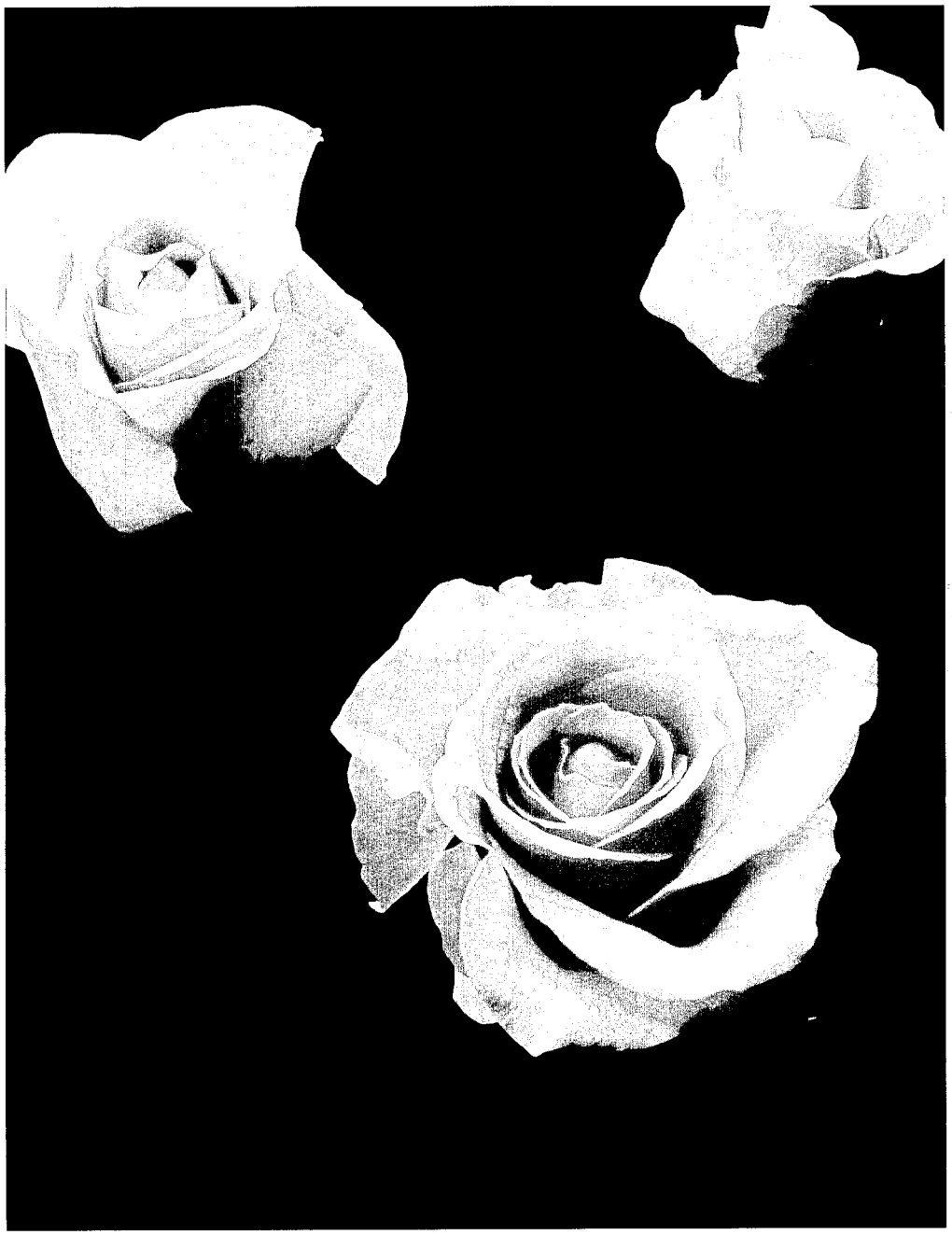

* * * * *